(12) United States Patent
Tanaka et al.

(10) Patent No.: US 9,341,461 B2
(45) Date of Patent: May 17, 2016

(54) WALL THICKNESS INSPECTION DEVICE

(71) Applicant: NIHON YAMAMURA GLASS CO., LTD., Amagasaki-shi, Hyogo (JP)

(72) Inventors: Naohiro Tanaka, Amagasaki (JP); Goro Tambo, Amagasaki (JP)

(73) Assignee: NIHON YAMAMURA GLASS CO., LTD., Hyogo (JP)

( * ) Notice: Subject to any disclaimer, the term of this patent is extended or adjusted under 35 U.S.C. 154(b) by 0 days.

(21) Appl. No.: 14/432,196

(22) PCT Filed: Sep. 24, 2013

(86) PCT No.: PCT/JP2013/075630
§ 371 (c)(1),
(2) Date: Mar. 28, 2015

(87) PCT Pub. No.: WO2014/050782
PCT Pub. Date: Apr. 3, 2014

(65) Prior Publication Data
US 2015/0276370 A1    Oct. 1, 2015

(30) Foreign Application Priority Data
Sep. 28, 2012  (JP) ................................. 2012-217308

(51) Int. Cl.
*G01R 27/26* (2006.01)
*G01B 7/06* (2006.01)
*G01N 27/22* (2006.01)

(52) U.S. Cl.
CPC ............... *G01B 7/08* (2013.01); *G01N 27/221* (2013.01)

(58) Field of Classification Search
CPC . G01N 27/221; G01N 27/22; B65H 2511/13; G01B 7/023; G01B 7/06
USPC .......................... 324/671, 600, 649, 658, 663
See application file for complete search history.

(56) References Cited

U.S. PATENT DOCUMENTS 4,820,972 A * 4/1989 Scott ...................... B07C 5/128
324/687

(Continued)

FOREIGN PATENT DOCUMENTS

| EP | 0544022 A1 | 6/1993 |
| JP | S64-25001 A | 1/1989 |

(Continued)

*Primary Examiner* — Tung X Nguyen
*Assistant Examiner* — Giovanni Astacio-Oquendo
(74) *Attorney, Agent, or Firm* — Rabin & Berdo, P.C.

(57) ABSTRACT

A wall thickness inspection device includes an electrostatic capacity detector 4 for detecting the electrostatic capacity of a portion of an object subjected to wall thickness inspection, and an arithmetic and control unit for taking in the electrostatic capacity detected by the electrostatic capacity detector 4 and converting the electrostatic capacity to a wall thickness. The electrostatic capacity detector 4 includes a sensor unit 5 brought into contact with the surface of a portion of the object subjected to the wall thickness inspection, and an elastic body 6 for biasing the sensor unit 5 toward the portion of the object. The sensor unit 5 has a curved surface 50 with the radius of curvature R represented by $2 \text{ mm} \leq R \leq 10 \text{ mm}$. The curved surface 50 is formed by bonding an electrode sheet 7 made of synthetic resin having each electrode pattern formed thereon to a belt-like attachment substrate 51 so that at least the electrode pattern of a measurement electrode from among the electrode pattern of the measurement electrode and the electrode pattern of an earth electrode is positioned on the surface of a curved portion of the attachment substrate 51.

3 Claims, 14 Drawing Sheets

(56) References Cited

U.S. PATENT DOCUMENTS

| | | | | |
|---|---|---|---|---|
| 5,097,216 A | * | 3/1992 | Dimmick, Sr. | G01B 7/287 209/522 |
| 5,139,406 A | * | 8/1992 | Hoshino | B29C 49/78 250/223 B |
| 5,558,233 A | | 9/1996 | Dimmick et al. | |
| 2009/0112509 A1 | * | 4/2009 | Batzinger | G01B 5/12 702/156 |

FOREIGN PATENT DOCUMENTS

| | | |
|---|---|---|
| JP | 2001-082908 A | 3/2001 |
| JP | 3416084 B2 | 6/2003 |

\* cited by examiner

Fig.9
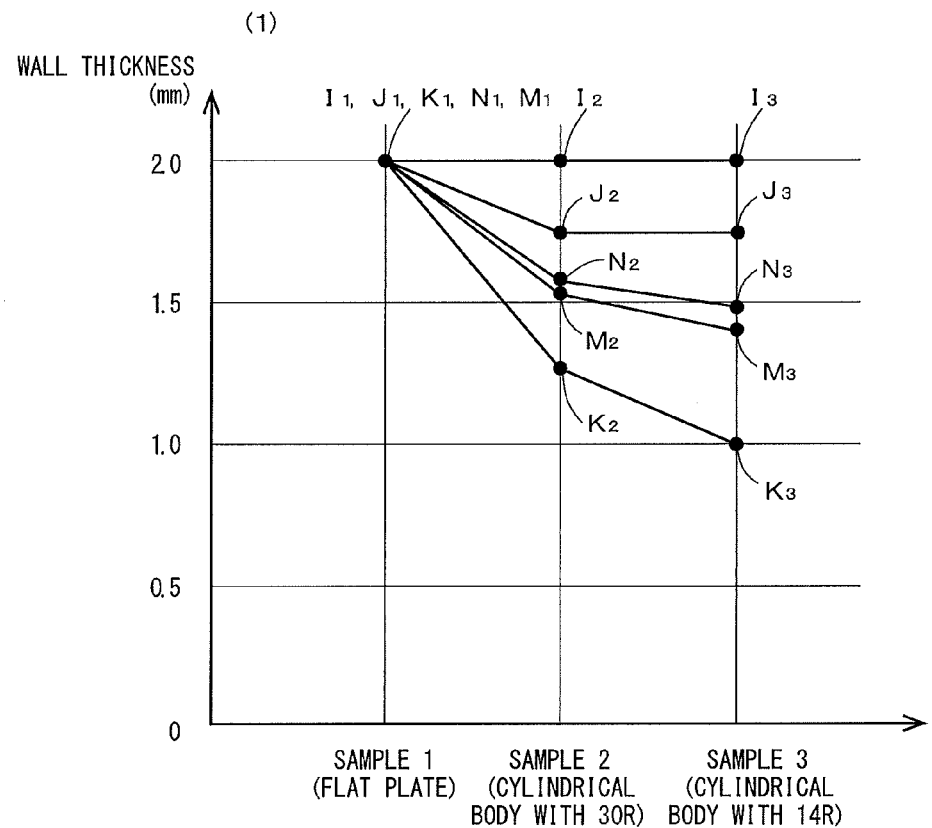
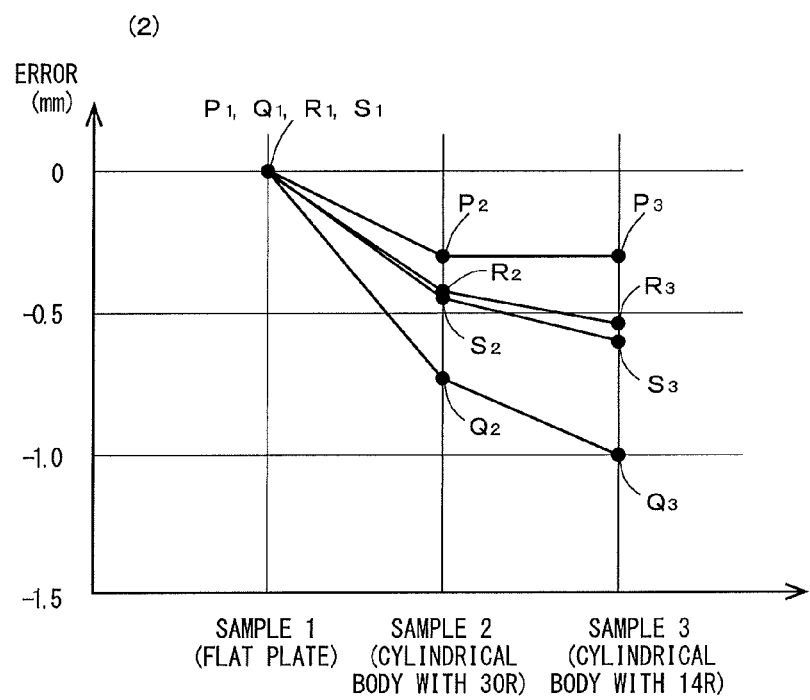

Fig.10
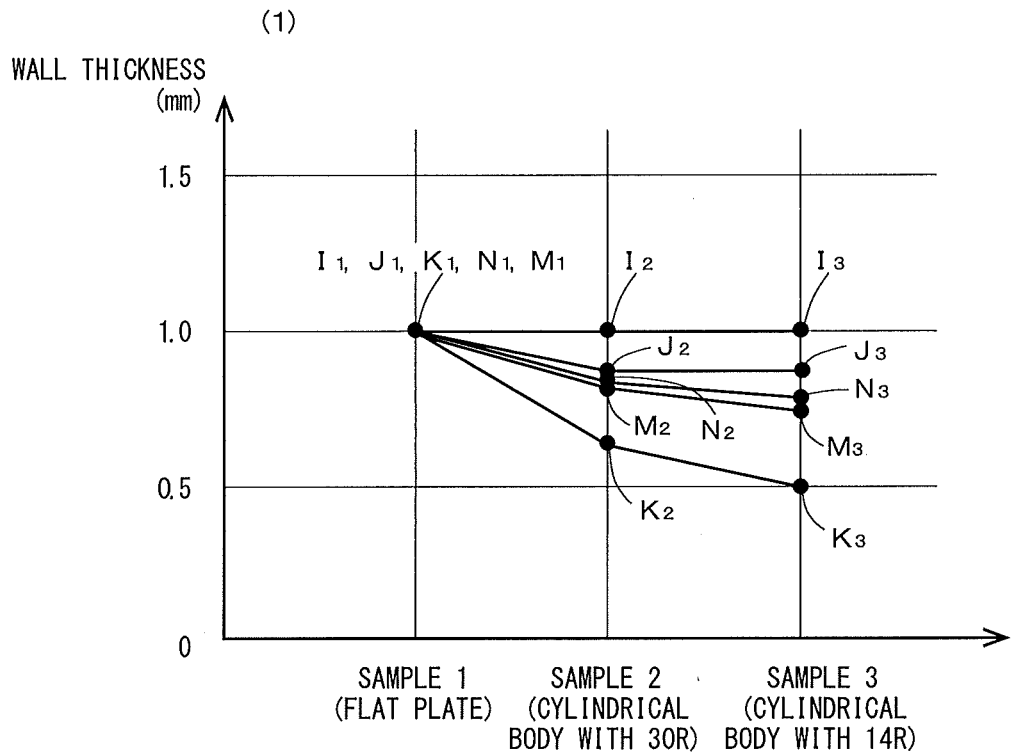
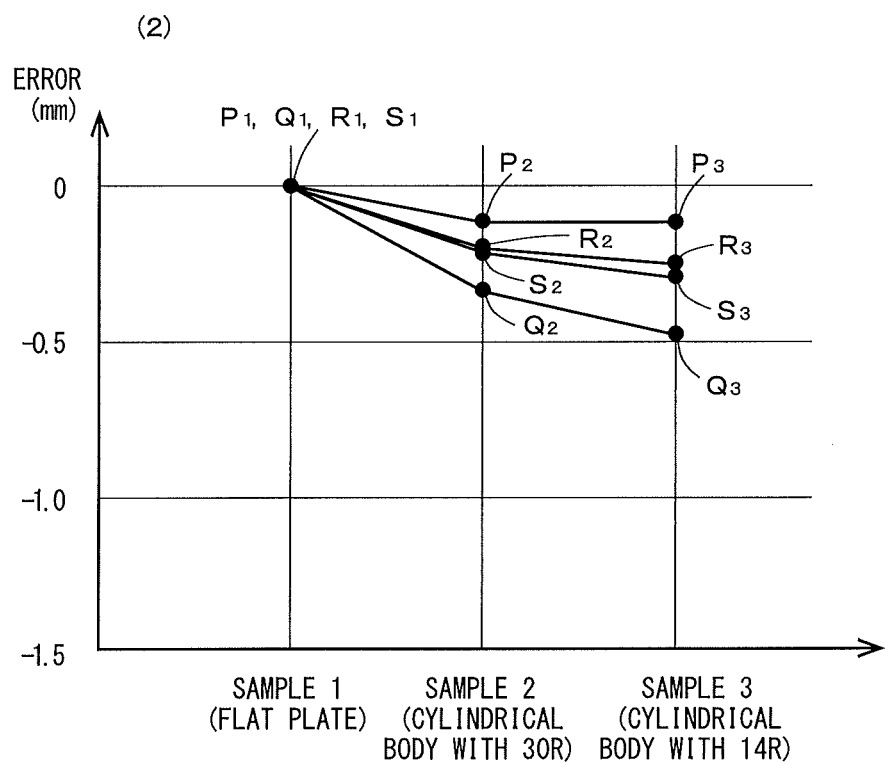

WALL THICKNESS INSPECTION DEVICE

FIELD OF THE INVENTION

The present invention relates to a wall thickness inspection device for inspecting the wall thickness of a portion of an object to be inspected such as a bottle by bringing a sensor into contact with the portion of the surface of the object. Specifically, the present invention relates to a wall thickness inspection device capable of accurately inspecting the wall thickness of a bottle even if the body of the bottle has a peripheral surface with no uniform degree of curvature over the entire periphery along the circumferential direction, such as a bottle which, when planarly viewed, has a body formed into a square shape (hereinafter, referred to as "square bottle") or into an ellipse shape (hereinafter, referred to as "ellipse bottle").

BACKGROUND OF THE INVENTION

For example, bottles are successively manufactured via a plurality of sections of bottle making machines in a bottle manufacturing plant. While being conveyed to a final stage of wrapping process, the bottles pass through inspection lines, and inspection for the presence or absence of defects and so forth are carried out. As a bottle inspection device installed in this type of inspection line, a plurality of inspection stations is arranged around a star wheel. A star wheel 8 illustrated in FIG. 17 is provided with a plurality of recesses 80 on the outer peripheral surface, and a bottle 10 introduced into each recess 80 is sequentially fed to each inspection station in accordance with the intermittent rotation of the star wheel 8. In an inspection station for inspecting the wall thickness of the bottle 10, the bottle 10 to be inspected is supported at the rotational center on the upper surface of a support table, and by axially rotating the bottle 10 around the central axis using a rotary drive mechanism, the wall thickness of the bottle 10 is measured over the entire periphery thereof, and thus the quality of the bottle 10 is determined.

An electrostatic capacity detector 9 is used as this type of wall thickness inspection device, for detecting the electrostatic capacity between the electrode pattern of a measuring electrode and the electrode pattern of an earth electrode with a sensor unit 90 brought into contact with the surface of the bottle 10 (for example, refer to a patent document 1). The electrostatic capacity detector 9 is provided with an elastic body 91 which pushes the sensor unit 90 toward the surface of the bottle 10, and thus even if the bottle 10 is vibrated, the elastic body 91 absorbs the vibration to stably maintain the contact state between the sensor unit 90 and the surface of the bottle 10.

The sensor unit 90 is formed by bonding an electrode sheet 93 made of synthetic resin, which has an electrode pattern formed thereon, to the surface of a belt-like attachment substrate 92 curved over the entire length. An electrostatic capacity of a portion of the bottle 10 with which the sensor unit 90 is brought into contact is detected between the electrode pattern of the measuring electrode and the electrode pattern of the earth electrode, while the detection output of the electrostatic capacity is introduced into an arithmetic and control unit (not shown) and converted into a wall thickness.

RELATED ART

Patent Document

[Patent Document 1]
Publication of Japanese patent No. 3416084

SUMMARY OF THE INVENTION

Problem to be Solved by the Invention

When an object to be inspected is a round bottle 10 with a cylindrical body as shown in FIG. 17, the degree of curvature of the peripheral surface of the body along the circumferential direction is uniform over the entire periphery of the bottle 10. For this reason, the contact state between the sensor unit 90 and the outer peripheral surface of the bottle 10 is maintained to be constant. In contrast, if the object to be inspected is a square bottle 10A as shown in FIGS. 18, 19, the degree of curvature of the peripheral surface of the body along the circumferential direction is not uniform over the entire periphery of the bottle 10A. Therefore, the relative positional relationship between the surface of the square bottle 10A and the electrode pattern of the sensor unit 90 is varied between a state where the sensor unit 90 comes in contact with a facing portion 11 which is almost flat with a small degree of curvature (shown in FIG. 18(1)) and a state where the sensor unit 90 comes in contact with a corner portion with a large degree of curvature (shown in FIG. 18(2), 18(3)). As a result, even if the wall thickness of the square bottle 10A is uniform over the entire periphery, the detected electrostatic capacities have different values depending on the portions of a bottle so that the wall thickness of the square bottle 10A is erroneously recognized.

Similarly, in a case where an object to be inspected is an ellipse bottle 10B as shown in FIG. 20, the degree of curvature of the peripheral surface of the body along the circumferential direction is not uniform over the entire periphery of the bottle 10B. Therefore, the relative positional relationship between the surface of the ellipse bottle 10B and the electrode pattern of the sensor unit 90 is varied between a state where the sensor unit 90 comes in contact with a gently curved short diameter portion 13 and a state where the sensor unit 90 comes in contact with a steeply curved long diameter portion 14. As a result, even if the wall thickness of the ellipse bottle 10B is uniform over the entire periphery, the detected electrostatic capacities have different values depending on the portions.

FIGS. 21(1), 21(2) illustrate the measurement results of the wall thickness at the upper end portion of the body of the square bottle 10A over the entire periphery. In FIG. 21(1), a line graph I shows measured values of the wall thickness of a bottle over the entire periphery (hereinafter, referred to as "reference value") which were acquired by measuring the wall thickness of the square bottle 10A at every prescribed angle with a mechanical gauge (for example, dial thickness gauge 100 described below), and a line graph K shows measured values of the wall thickness of a bottle over the entire periphery which were acquired by measuring the wall thickness of the square bottle 10A at every prescribed angle with a wall thickness inspection device using an electrostatic capacitor detector 9 shown in FIG. 17. Further, in FIG. 21(2), a line graph Q shows measurement errors at every angle for the measured values K with respect to the reference values I. The measurement errors at the facing portions 11 have small values, whereas the measurement errors at the corner portions 12 have large values.

FIGS. 22(1), 22(2) illustrate the measurement results of the wall thickness at the lower end portion of the body of the square bottle 10A over the entire periphery. In FIG. 22(1), 22(2) a line graph I shows measured values of the wall thickness of a bottle over the entire periphery (hereinafter, referred to as "reference value") which were acquired by measuring the wall thickness of the square bottle 10A at every prescribed angle with a mechanical gauge (for example, dial thickness gauge 100 described below), and a line graph K shows measured values of the wall thickness of a bottle over the entire periphery which were acquired by measuring the wall thickness of the square bottle 10A at every prescribed angle with a wall thickness inspection device using an electrostatic capacitor detector 9 shown in FIG. 17. Further, a line graph Q shows measurement errors at every angle for the measured values K with respect to the reference values I. The measurement errors at the facing portions 11 have small values, whereas the measurement errors at the corner portions 12 have large values.

Although not shown in the drawings, errors in measurement of wall thickness differs depending on the portion of measurement even for the ellipse bottle 10B so that the measurement errors at the steeply curved long diameter portion 14 becomes larger than the measurement errors at the gently curved short diameter portion 13.

Further, when the square bottle 10A transitions from a state where the sensor unit is in contact with the facing portion 11 (a state shown in FIG. 18(1)) to a state where the sensor unit is in contact with the corner portion 12 (a state shown in FIG. 18(3)), the sensor unit 90 is pulled in a rotational direction of the square bottle 10A (shown in an arrow a in the drawings) so that the elastic body 91 might be compressed and deformed while being distorted in the rotational direction a. When such a deformation occurs, the contact position where the sensor unit 90 is in contact with the facing portion 11 is changed from the contact position where the sensor unit 90 is in contact with the corner portion 12 on the outer peripheral surface of the bottle 10A. The deformation not only causes variation in the measurement values of wall thickness, but also causes a problem that the sensor unit 90 cannot follow the rotation of the square bottle 10A when the contact position where the sensor unit 90 is in contact with the outer peripheral surface of the bottle 10A subsequently transitions from the corner portion 12 to the facing portion 11. This is because the elastic restoring force of the elastic body 91 is not sufficient in a case wherein the difference in curvature between the facing portion 11 and the corner portion 12 in the bottle 10A is large, or even if the difference is small, the rotational speed of the bottle 10A is large. For this reason, a phenomenon that the sensor unit 90 loses touch with the outer peripheral surface of the square bottle 10A (hereinafter, referred to as "jumping phenomenon") might occur so that portions where wall thickness cannot be measured (shown in dotted lines in the drawings) might be generated.

The present invention has been made in view of the above-mentioned problem, and the objective of the invention is to provide a wall thickness inspection device capable of accurately inspecting the wall thickness of a bottle over the entire periphery with little change in relative positional relationship between the surface of an object to be inspected and an electrode pattern even if the object to be inspected fails to have a constant degree of curvature for the peripheral surface over the entire periphery of the body portion along the circumferential direction such as a square bottle or an ellipse bottle.

Another objective of the present invention is to provide a wall thickness inspection device which does not cause a jumping phenomenon that the sensor unit might lose touch with the outer peripheral surface of a portion of the object subjected to the wall thickness inspection.

Means for Solving the Problem

A wall thickness inspection device according to the present invention includes an electrostatic capacity detector for detecting the electrostatic capacity of a portion of an object subjected to wall thickness inspection, and an arithmetic and control unit for taking in the electrostatic capacity detected by the electrostatic capacity detector and converting the electrostatic capacity to a wall thickness. The electrostatic capacity detector includes a sensor unit brought into contact with the surface of a portion of the object subjected to the wall thickness inspection and an elastic body for biasing the sensor unit toward the portion of the object. The sensor unit has a curved surface which has the radius of curvature R represented by 2 mm≤R≤10 mm. The curved surface is formed by bonding an electrode sheet made of synthetic resin having each electrode pattern formed thereon to a belt-like attachment substrate so that at least the electrode pattern of a measurement electrode from among the electrode pattern of the measurement electrode and the electrode pattern of an earth electrode is positioned on the surface of a curved portion of the attachment substrate.

For example, when the wall thickness of a bottle is inspected using the wall thickness inspection device having the above-mentioned configuration, the radius of curvature R of the sensor unit is set to the least possible value, and thus even if an object to be inspected might not have the peripheral surface of the body with the uniform degree of curvature along the circumferential direction over the entire periphery thereof as with a square bottle, the relative positional relationship between the surface of the object to be inspected and the electrode pattern of the sensor unit varies little between a state where the sensor unit is in contact with an almost flat facing portion having a small degree of curvature and a state where the sensor unit is in contact with a corner portion having a large degree of curvature. As a result, the detected values of electrostatic capacities can be prevented from varying depending on portions despite the fact that the wall thickness of the object to be inspected has the same value over the entire periphery, and thus it is possible to prevent erroneous recognition of wall thickness.

In a preferable embodiment according to the present invention, the electrode sheet is bonded to the attachment substrate from the front surface to the back surface thereof with each electrode pattern being formed so that the electrode pattern of the measurement electrode is located on the front surface of the attachment substrate and the electrode pattern of the earth electrode is located on the back surface of the attachment substrate.

According to this embodiment, a lot of electrical charges can be stored in a portion of an object subjected to wall thickness inspection compared to those that have both the electrode pattern of a measurement electrode and the electrode pattern of an earth electrode located on the front surface of an attachment substrate. As a result, measurement sensitivity for electrostatic capacity can be increased.

In a preferable embodiment according to the present invention, the elastic body is formed of fan-shaped sponge or open-cell foam having a constant thickness; the attachment substrate is bonded to a first side end surface of the elastic body with the curved portion facing outside; and a second side end surface of the elastic body is bonded to a printed circuit board so that the whole of the elastic body expands and contracts with the pivot of the fan as a fulcrum.

In this embodiment, for example, in a case where the sensor unit is brought into contact with the outer peripheral surface of a square bottle, when the state of the sensor unit in contact with the surface of the bottle transitions from a state where the sensor unit is in contact with the facing surface portion of the bottle to a state where the sensor unit is in contact with the corner portion in accordance with the rotation of the square bottle, even if the sensor unit is pulled in the rotational direction of the bottle, the whole of the elastic body is compressed and deformed with the fulcrum as the center without being warped in the rotational direction. Therefore, the contact position of the sensor unit with respect to the outer peripheral surface of the square bottle is almost the same whether the contact position is on the corner portion or the facing surface portion. Further, when the contact position of the sensor unit with respect to the outer peripheral surface of the square bottle transitions from the corner portion to the facing surface portion, since the elastic body is compressed and deformed without being warped in the rotational direction, the restoring force of the elastic body will never be lost. The restoring force effectively acts on the direction toward the square bottle, and as a result, the sensor unit moves following the rotation of the square bottle, so that a jumping phenomenon that the sensor unit loses touch with the outer peripheral surface of the square bottle can be prevented.

Effect on the Invention

The present invention makes it possible to carry out accurate wall thickness inspection over the entire periphery of an object to be inspected even for bottles such as square bottles and ellipse bottles that do not have uniform degree of curvature in the circumferential direction of the peripheral surface of the body over the entire periphery without causing a significant change in the relative positional relationship between the surface of the object to be inspected and an electrode pattern.

Additionally, in a preferable embodiment, the elastic body is constituted using fan-shaped sponge or open-cell foam having a constant thickness, and thus a jumping phenomenon that a sensor unit loses touch with the surface of the object to be inspected can be prevented.

BRIEF DESCRIPTION OF THE DRAWINGS

FIG. 9 is a view illustrating measurement results and the measurement errors thereof of wall thickness for a plurality of types of samples having a thickness of 2 mm using a plurality of types of electrostatic capacity detectors.

FIG. 10 is a view illustrating measurement results and the measurement errors thereof of wall thickness for a plurality of types of samples having a thickness of 1 mm using a plurality of types of electrostatic capacity detectors.

MODE FOR CARRYING OUT THE INVENTION

Figure 1:
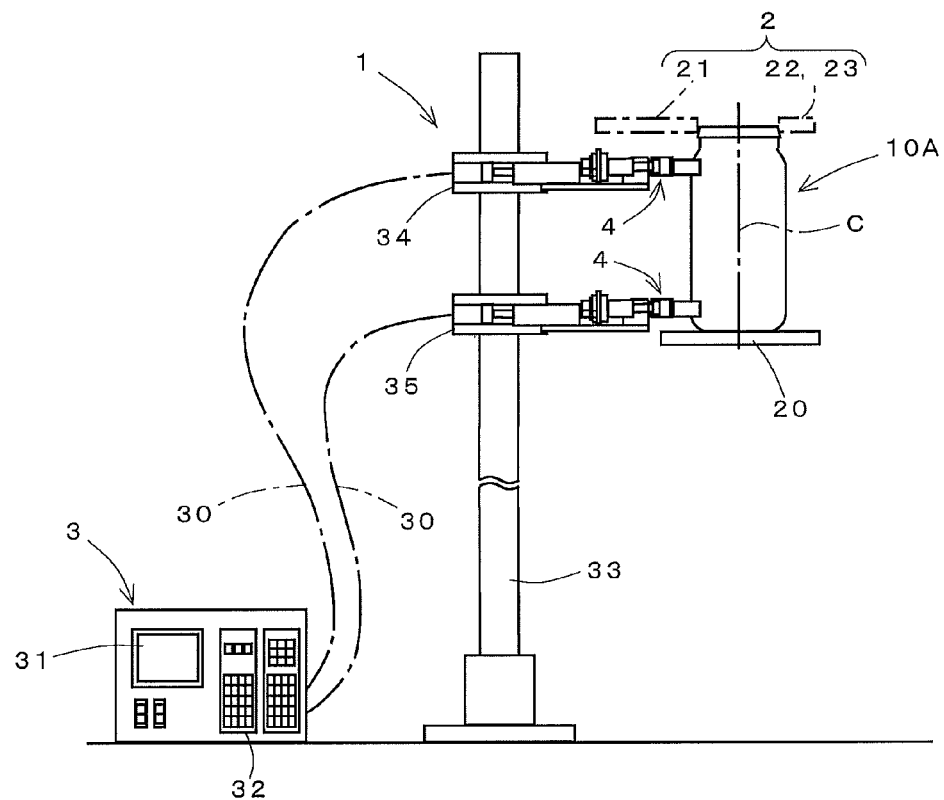
FIG. 1 is a front view illustrating a schematic block diagram of a wall thickness inspection device according to an embodiment of the present invention.

FIG. 1 shows an overall structure of a wall thickness inspection device 1 according to an embodiment of the present invention. The wall thickness inspection device 1 illustrated in the drawing is used for inspecting the wall thickness of a glass bottle, but not limited to this, the wall thickness inspection device 1 can be used for inspecting the wall thickness of a synthetic resin bottle. Also, it is possible to inspect not only the wall thickness of a bottle but also the wall thickness of various types of containers, and the wall thickness of a plate-like body.

Figure 19:
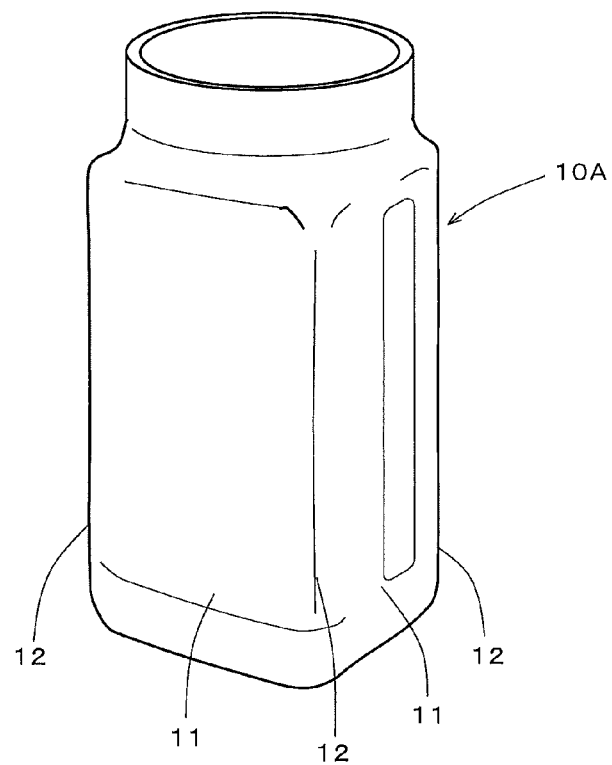
FIG. 19 is a perspective view illustrating a sample of a square bottle.
Figure 20:
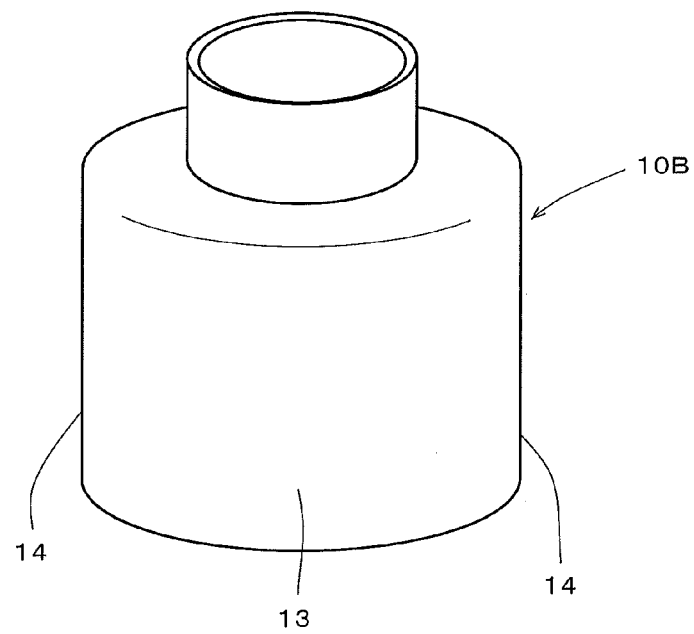
FIG. 20 is a perspective view illustrating a sample of an ellipse bottle.
Figure 21:
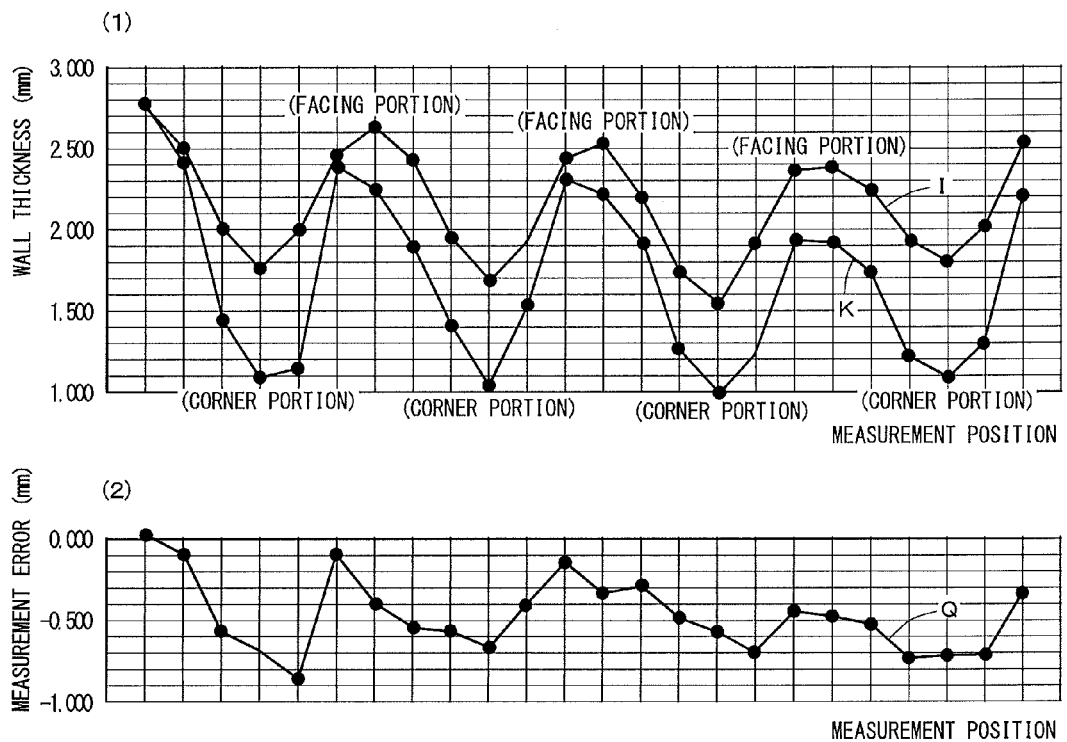
FIG. 21 is a view for illustrating measurement results of a wall thickness for the upper end portion of the body of a square bottle using a conventional electrostatic capacity detector.
Figure 22:
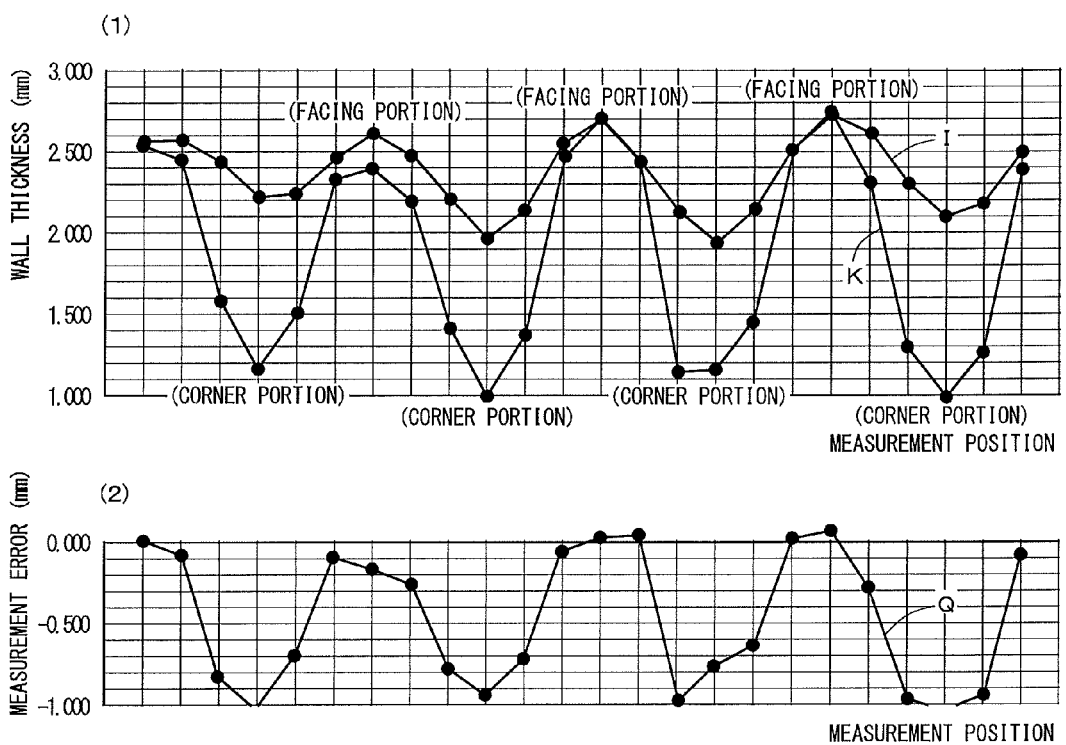
FIG. 22 is a view for illustrating measurement results of a wall thickness for the lower end portion of the body of a square bottle using a conventional electrostatic capacity detector.

The wall thickness inspection device 1 shown in the drawing inspects the square bottle 10A shown in FIG. 19, which is placed at any one of a plurality of inspection stations provided around a star wheel (not shown). The wall thickness inspection device 1 as an illustrated example is suitable for the wall thickness inspection of the square bottle 10A, but it is also preferably suitable for the wall thickness inspection of the ellipse bottle 10B shown in FIG. 20. Additionally, the shape of the body of the square bottle 10A is not limited to quadrilaterals in a plan view, but may include pentagons, hexagons and so forth. A plurality of recesses is provided on the outer peripheral surface of the star wheel, and square bottles 10A (hereinafter, simply referred to as "bottle") introduced into each recess are sequentially fed to each inspection station while being restrained in the recesses in accordance with the intermittent rotation of the star wheel.

In an inspection station where the wall thickness inspection device 1 is installed, the bottle 10A to be inspected is supported on the center of rotation of a horizontal and rotatable support table 20. The bottle 10A is axially rotated around the central axis c of the bottle 10A by a rotary drive mechanism 2, thereby the wall thickness of the bottle 10A is inspected over the entire periphery. The rotary drive mechanism 2 in the illustrated example is constituted by the support table 20, a drive roller 21 brought into contact with the outer peripheral surface of the mouth of the bottle 10A supported on the support table 20 for rotating the bottle 10A with a frictional force during rotation, a pair of driven rollers 22, 23 for supporting the mouth of the bottle 10A interposed between the drive roller and the driven rollers 22, 23, and a drive device (not shown) for rotating the drive roller 21. The rotary drive mechanism 2 may directly rotate the support table 20.

FIG. 1 shows a state where the wall thickness of the bottle 10A is measured and inspected concurrently at two positions of the upper portion and the lower portion of the body. However, the wall thickness may be measured at a single position or three or more positions. When measuring the wall thickness concurrently at two positions, two electrostatic capacity detectors 4, 4 are connected to a main body 3 of the device via wire cords 30, 30 respectively. A monitor 31 for displaying various types of data such as inspection results, and an operation unit 32 whereon a plurality of key switches, display lamps and so on is disposed are provided on the front face of the main body 3. Each electrostatic capacity detector 4 is respectively secured to fixing tables 34, 35 that are provided liftably along a vertically erected mounting stand 33. The detection outputs as analog values detected by each electrostatic capacity detector 4, 4 are sampled at a prescribed sampling cycle and converted to digital values, thereafter taken in an arithmetic and control unit incorporated into the main body 3 of the device.

Figure 8:
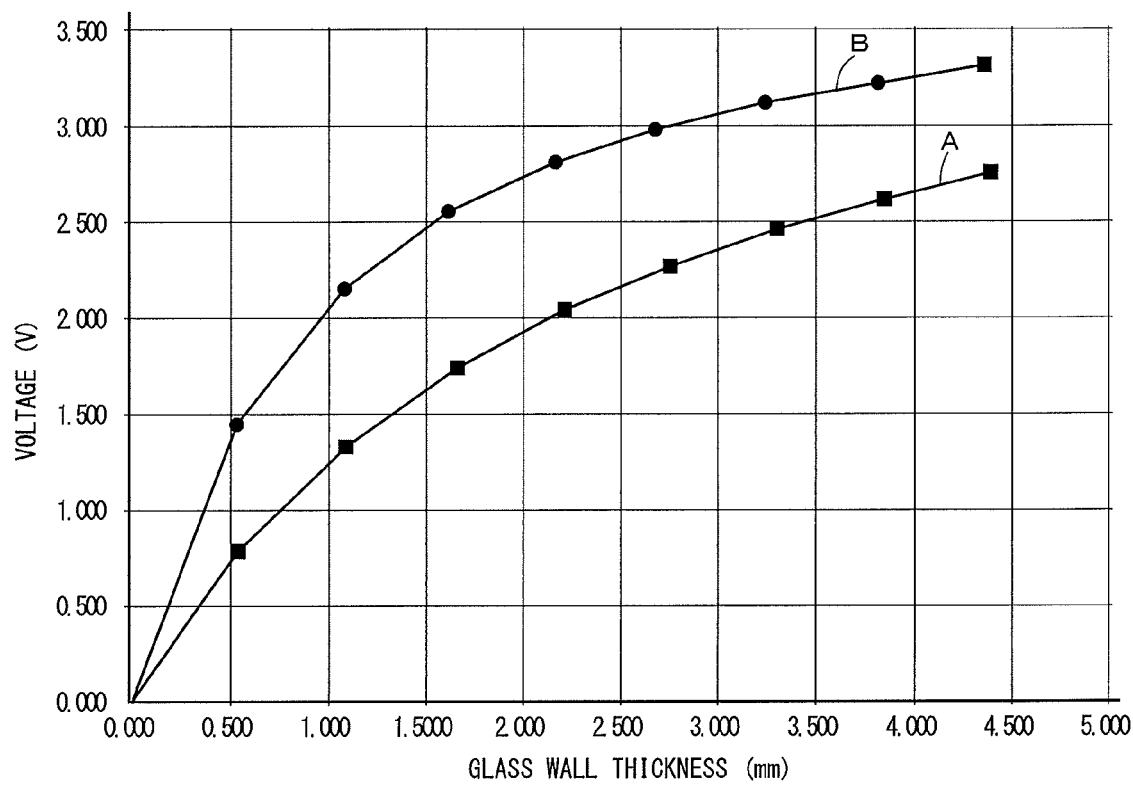
FIG. 8 is a view illustrating a wall thickness conversion curve for converting detected electrostatic capacities to wall thicknesses.

The arithmetic and control unit not shown converts each sample data of detection output from the electrostatic capacity detector 4 to wall thickness on the basis of a wall thickness conversion curves A, B as shown in FIG. 8 (details are described later). Further, the arithmetic and control unit serially controls the input-output operation of the operation unit 32 and controls the display operation of the monitor 31. The arithmetic and control unit includes a microprocessor for carrying out computation and control and a memory and the like for storing programs and data. The memory stores conversion data constituting the wall thickness conversion curves A, B. The microprocessor converts each sample data of detection output from the electrostatic capacity detector 4 corresponding to one rotation of the bottle 10A respectively to each wall thickness with reference to the memory and stores the wall thickness in the memory, while displaying the storage data on the monitor 31.

Figure 2:
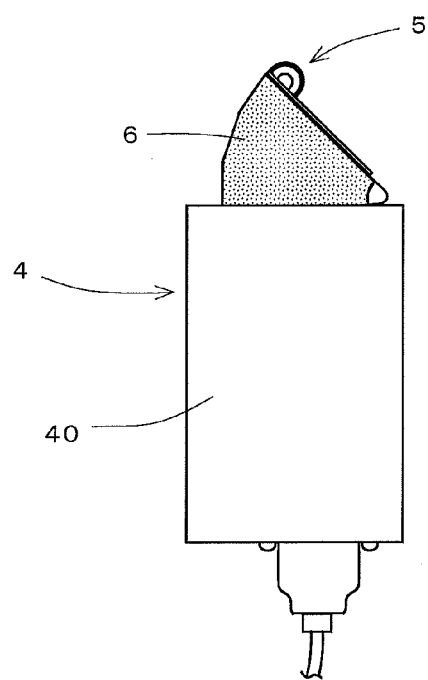
FIG. 2 is a front view illustrating a structure of an electrostatic capacity detector.
Figure 3:
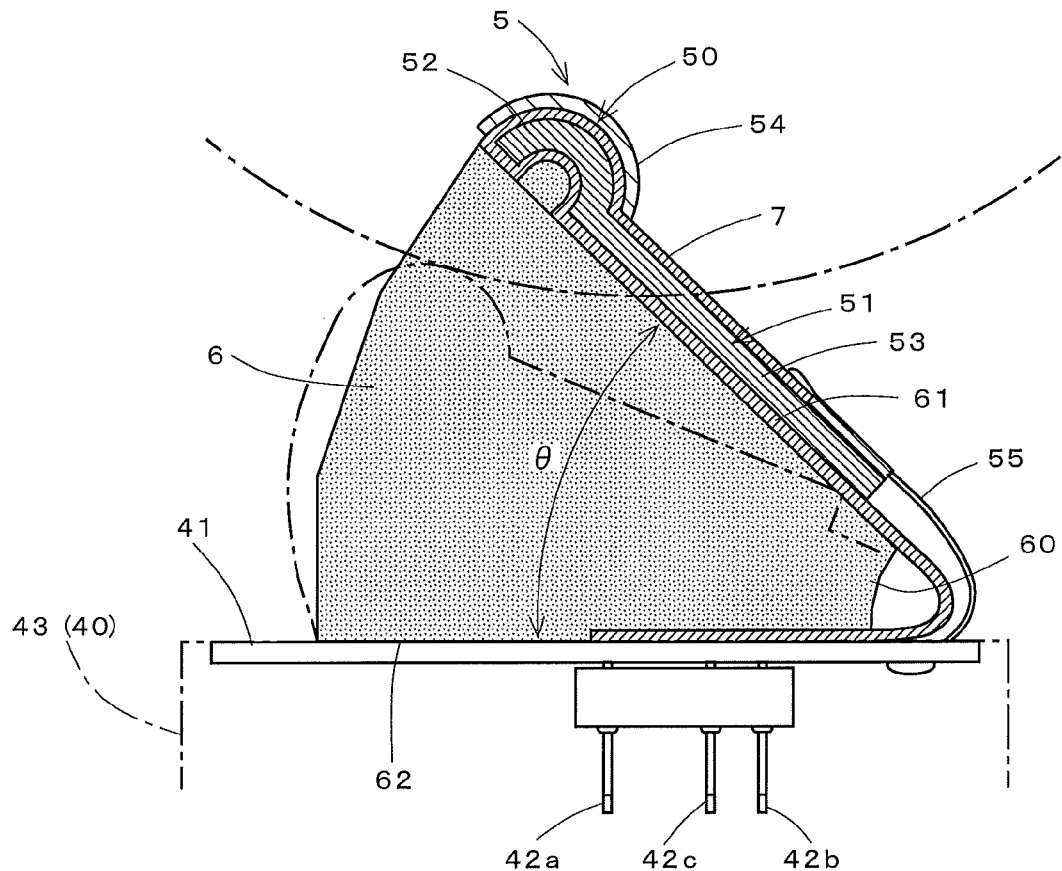
FIG. 3 is an enlarged side view illustrating a structure of a sensor unit in an electrostatic capacity detector.

Each electrostatic capacity detector 4 detects an electrostatic capacity on a portion brought into contact with the bottle 10A axially rotated on the support table 20. As shown in FIGS. 2, 3, each electrostatic capacity detector 4 is constituted by a sensor unit 5 brought into contact with the surface of the bottle 10A, an elastic body 6 for pushing the sensor unit 5 toward the surface of the bottle 10A, and a detector main body 40. The detector main body 40 incorporates an electrostatic capacity detection circuit therein which is electrically connected via a printed circuit board 41 and three connector pins 42a to 42c to the electrode pattern (details are describe later) on a electrode sheet 7 which is made of synthetic resin and constitutes the sensor unit 5.

The sensor unit 5 includes a curved surface 50 having a prescribed radius of curvature R. The curved surface of the sensor unit 5A is covered with a protective film 54 for protecting the electrode sheet 7 described later. The curved surface 50 is constituted by bending the flexible electrode sheet 7 into an arc shape and bonding the electrode sheet 7 to the surface of a curved portion 52 formed at one end of a belt-like attachment substrate 51 so that an electrode pattern 71 (to be described later) of a measurement electrode is located at surface of the curved portion 52. The radius of curvature R of the curved surface 50 is preferably set to the least possible value, and is set to 4 mm in this embodiment. However, the curved surface 50 can be manufactured as long as the radius of curvature R is defined as 2 mm≤R≤10 mm and the above-mentioned measurement errors are practically permissible. Setting the radius of curvature R to 2 mm or greater and 10 mm or lower will be described later. The above-described electrode sheet 7 is formed into a belt-like shape with a constant width almost over the entire length as shown in FIG. 4, and is bonded to both the front side and the back side of the curved portion 52 and a flat portion 53 of the attachment substrate 51.

The elastic body 6 is formed of fan-shaped sponge or open-cell foam having a constant thickness. When a pressing force acts on the curved surface 50 of the sensor unit 5, the whole of the elastic body 6 contracts so that the angle θ made by both side end surfaces 61, 62 is decreased with the pivot of the fan as a fulcrum 60 and with the fulcrum 60 as the center. The attachment substrate 51 is bonded to a first side end surface 61 of the elastic body 6 with the sensor unit 5 facing outside. A second side end surface 62 of the elastic body 6 is bonded to the upper surface of a belt-like printed circuit board 41 mounted above an opening of a case body 43 constituting the detector main body 40.

Figure 4:
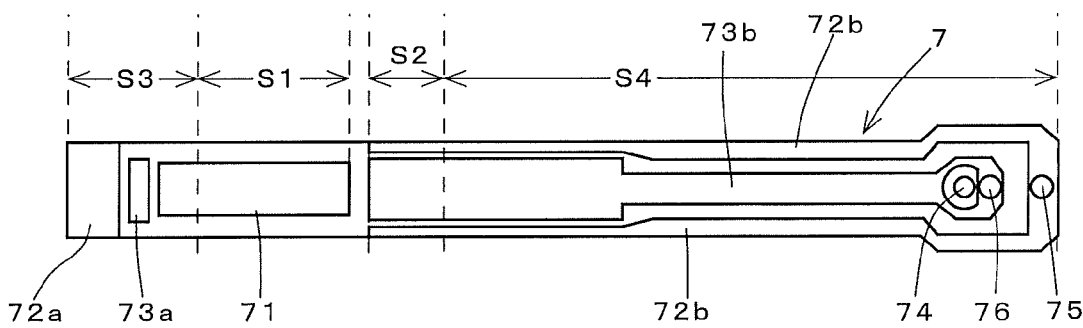
FIG. 4 is a plan view illustrating an electrode pattern formed on an electrode sheet.

The electrode sheet 7 shows an electrode pattern of a measurement electrode (hereinafter, referred to as "measurement electrode pattern") 71 and electrode patterns of an earth electrode (hereinafter, referred to as "earth electrode pattern") 72a, 72b as shown in FIG. 4. Further, in this embodiment, FIG. 4 shows electrode patterns of a guard electrode (hereinafter, referred to as "guard electrode pattern") 73a, 73b for suppressing the influence of electrostatic capacities from the outside excluding the bottle 10A.

In FIG. 4, S1 is an area which is positioned at and secured to the front surface of the curved portion 52 of the attachment substrate 51, and only the measurement electrode pattern 71 exists in the area S1. S2 is an area which is positioned and secured along the back surface of the curved portion 52, and the guard electrode pattern 73b and the earth electrode patterns 72b, 72b that sandwich the guard electrode pattern 73b exist in the area S2. S3 is an area which is positioned and secured along the front surface of the flat portion 53 of the attachment substrate 51, the measurement electrode pattern 71, the guard electrode pattern 73a, and the earth electrode pattern 72a exist in this area S3. S4 is an area which is positioned and secured along the back surface of the flat portion 53 of the attachment substrate 51 and along the front surface of the printed circuit board 41 the measurement electrode pattern 71, the guard electrode pattern 73b and the earth electrode patterns 72b, 72b that sandwich the guard electrode pattern 73b exist in this area S4. Further, connection patterns 74 to 76 conducted with three connector pins 42a to 42c are formed at the end of the area S4.

Figure 5:
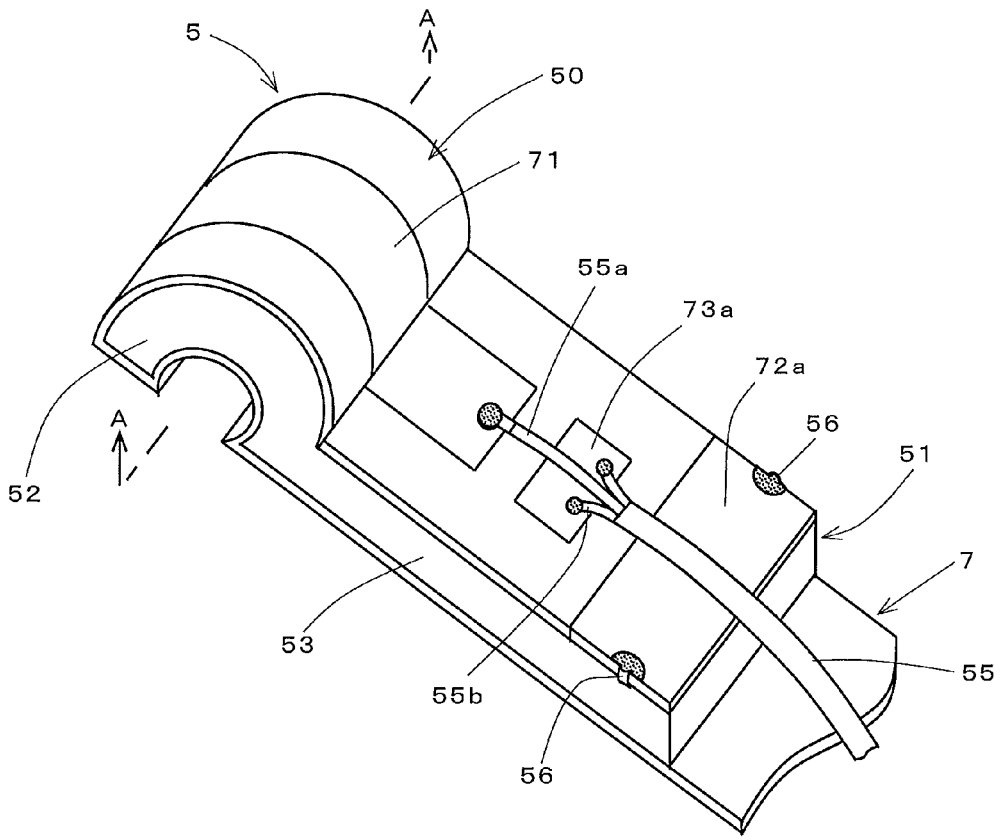
FIG. 5 is an enlarged perspective view illustrating a state where an electrode sheet is bonded to an attachment substrate.
Figure 6:
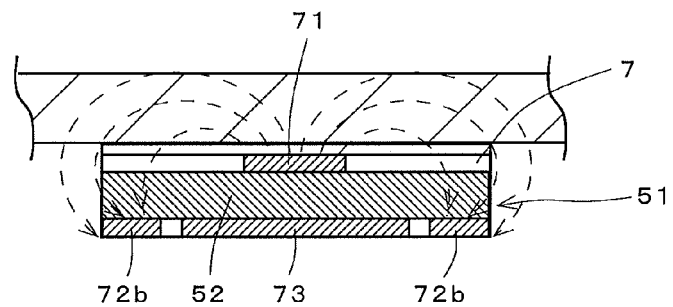
FIG. 6 is a cross-sectional view taken along a line A-A in FIG. 5.
Figure 7:
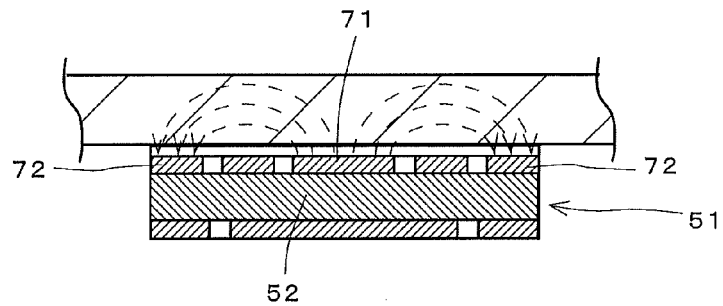
FIG. 7 is a cross-sectional view illustrating another embodiment of an electrode pattern.

In the curved portion 50 of the sensor unit 5, the measurement electrode pattern 71 is located in the center of the width as shown in FIG. 5 and FIG. 6. Further, the earth electrode pattern 72b is located on the back side of the curved portion 50, that is, at both side edges on the back surface of the curved portion 52 of the attachment substrate 51. According to this embodiment, compared to another embodiment shown in FIG. 7 wherein the earth electrode pattern 72 is located at both side edges of the front surface of the curved portion 52, a lot of electrical charges can be stored in a portion of the object subjected to wall thickness inspection with which the sensor unit 5 is brought into contact, and thus a measurement sensitivity for electrostatic capacity can be increased. Arrows drawn with dotted lines represent lines of electric force generated from the measurement electrode pattern 71 to the earth electrode pattern 72b (FIG. 6), (FIG. 7).

Lead wires 55a, 55b are connected to the measurement electrode pattern 71 and the guard electrode pattern 73a of the electrode sheet 7 located on the flat portion 53 of the attachment substrate 51. The two lead wires 55a, 55b are bundled together to form a single lead wire 55 which is guided to the back surface of the printed circuit board 41, and electrically connected to a conductive pattern (not shown) printed on the back surface of the printed circuit board 41. Further, the earth electrode pattern 72a on the flat portion 53 of the attachment substrate 51 is electrically conducted with the earth electrode patterns 72b, 72b at both sides on the back surface of the attachment substrate 51 via conductive wires 56, 56. The conductive pattern on the back surface of the printed circuit board 41 and the connection patterns 74 to 76 of the electrode sheet are conducted with connector pins 42a to 42c. Each connector pin 42a to 42c is connected to a connector incorporated inside the detector main body 40 (not shown). Thereby, the measurement electrode pattern 71, the earth electrode patterns 72a, 72b, and the guard electrode patterns 73a, 73b of the electrode sheet 7 are electrically connected with an electrostatic capacity detection circuit incorporated in the detector main body 40.

The electrostatic capacity detection circuit outputs a voltage value V corresponding to the electrostatic capacity of a portion of an object subjected to wall thickness inspection, that is, a portion with which the sensor unit 5 is brought into contact. The detection output is taken in the arithmetic and control unit incorporated in the device main body 3. The structure of an electrostatic capacity detection circuit is well known to the public as shown in the patent document 1 (Japanese patent No. 3416084), and thus the detailed description is omitted here.

Figure 17:
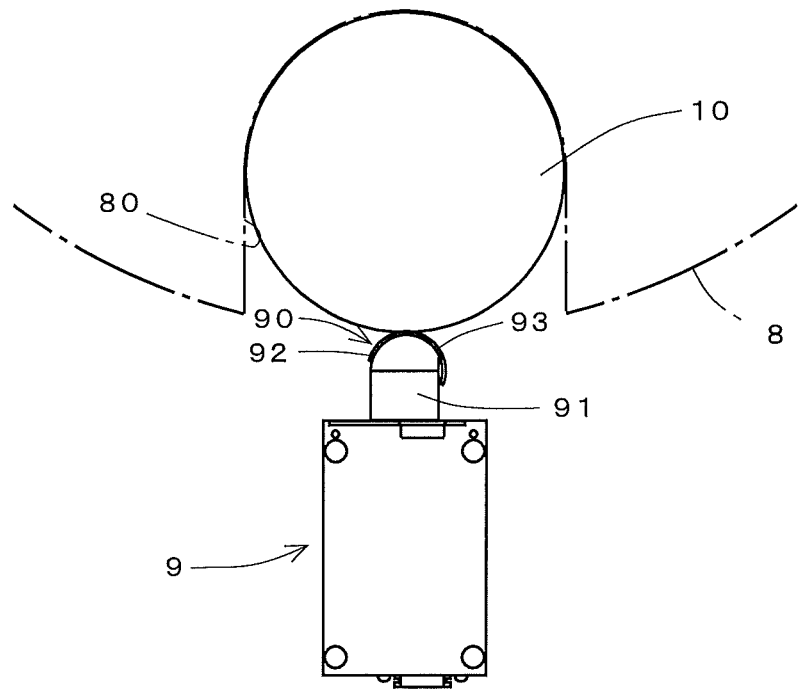
FIG. 17 is a plan view illustrating the structure of an electrostatic capacity detector used for a conventional wall thickness inspection device for a bottle.
Figure 18:
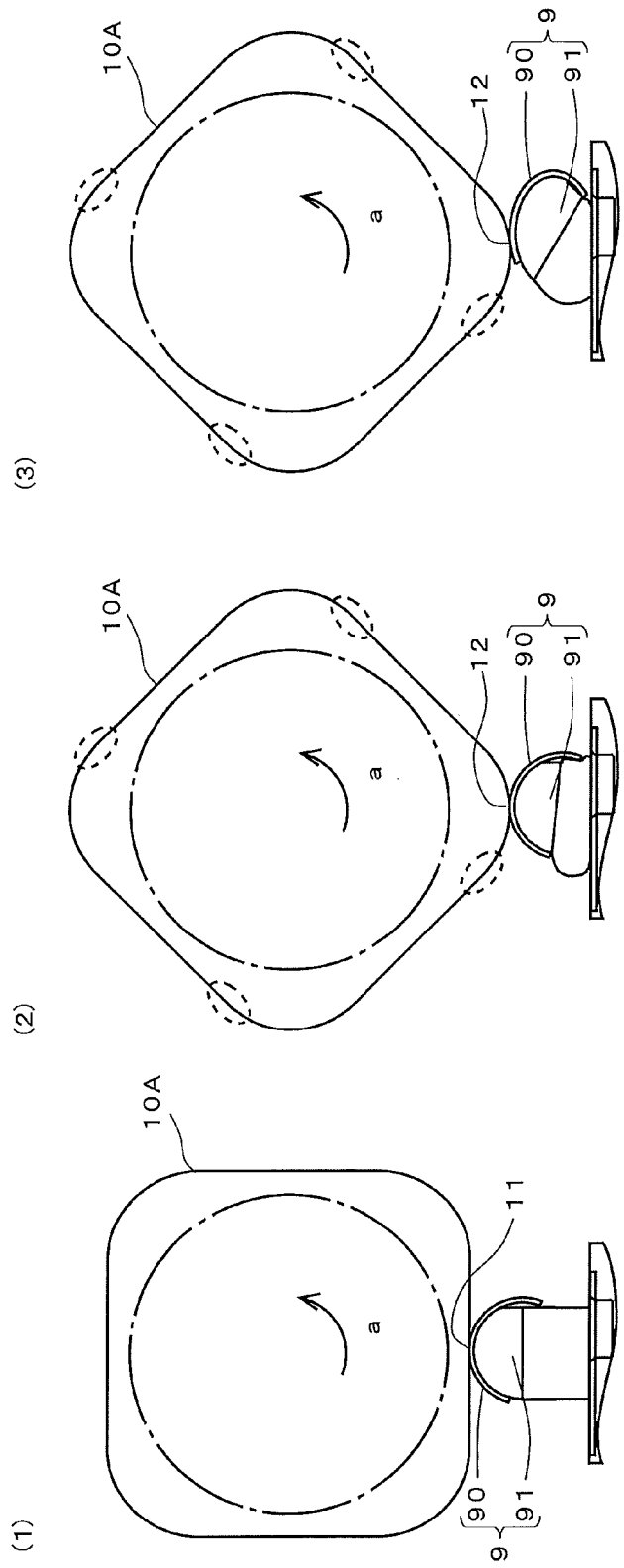
FIG. 18 is a plan view illustrating states of wall thickness inspection for a square bottle using the electrostatic capacity detector shown in FIG. 17.

FIG. 8 illustrates an example a wall thickness conversion curve used for converting the above-mentioned voltage value V to a wall thickness d in the arithmetic and control unit. A in the drawing represents a wall thickness conversion curve which is applied to an electrostatic capacity detector 4 (hereinafter, referred to as "new type electrostatic capacity detector 4") wherein the curved surface 50 in the sensor unit 5 has the radius of curvature R of 4 mm. B represents a wall thickness conversion curve which is applied to a conventional electrostatic capacity detector 9 (hereinafter, referred to as "old type electrostatic capacity detector 9") shown in FIG. 17. Both the wall thickness conversion curves A, B are calculated using each of the electrostatic capacity detector 4, 9, by multiplying measurement data acquired by measuring the wall thickness of plate glass having known thickness by a coefficient, and the coefficient is determined so that the multiplied value is an already known value of wall thickness. The old type electrostatic capacity detector 9 is mainly used for wall thickness inspection for bottles excluding the square bottle 10A and the ellipse bottle 10B, and the radius of curvature R is set to 17 mm for the curved surface of the sensor unit 90 of the old type electrostatic capacity detector 9 to which the wall thickness conversion curve B is applied.

FIG. 9(1) shows measurement results when measuring the wall thicknesses of samples 1 to 3 having a wall thickness of 2 mm, using a dial thickness gauge 100, new type electrostatic capacity detectors 4 and an old type electrostatic capacity detector 9, the new type electrostatic capacity detectors 4 having the radii of curvature of 4 mm, 8 mm, and 10 mm respectively for the curved surface 50 of the sensor unit 5. The sample 1 is made of a flat plate; the sample 2 is made of a cylindrical body with a radius of 30 mm; and the sample is made of a cylindrical body with a radius of 14 mm respectively.

In the drawing, $I_1$ to $I_3$ are measurement data (reference data) of wall thickness using a dial thickness gauge 100; $J_1$ to $J_3$ are measurement data of wall thickness using the new type electrostatic capacity detectors 4 having the radius of curvature R of 4 mm for the curved surface 50; $N_1$ to $N_3$ are measurement data of wall thickness using the new type electrostatic capacity detectors 4 having the radius of curvature R of 8 mm for the curved surface 50; $M_1$ to $M_3$ are measurement data of wall thickness using the new type electrostatic capacity detectors 4 having the radius of curvature R of 10 mm for the curved surface 50; and $K_1$ to $K_3$ are measurement data of wall thickness using the old type electrostatic capacity detector 9. Each sample 1 to 3 is made of synthetic resin, and the material is a polyvinylidene fluoride (PVDF) having a dielectric constant similar to a soda glass.

Figure 11:
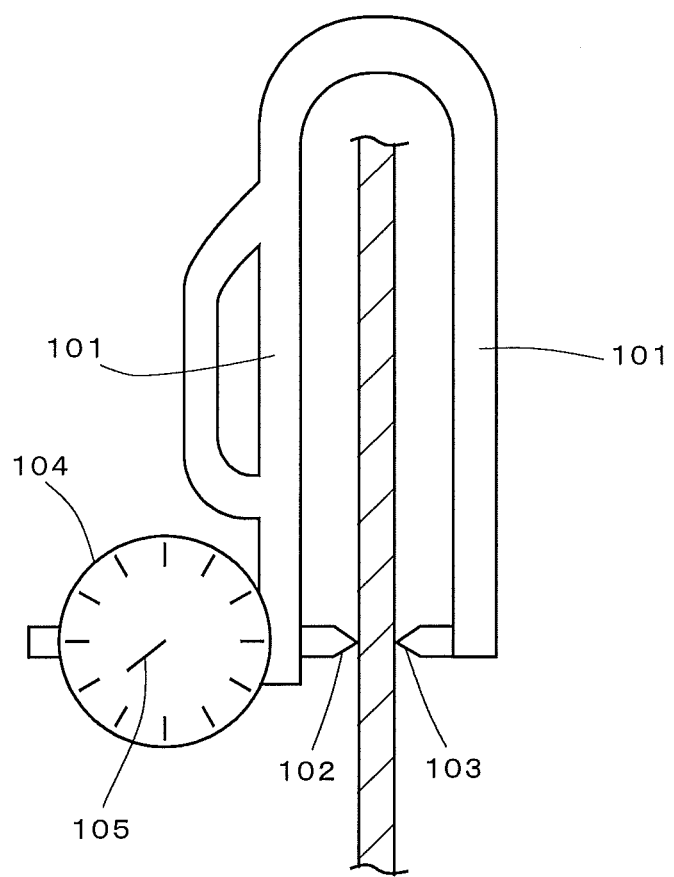
FIG. 11 is a front view illustrating the structure of a mechanical gauge used for measuring a wall thickness.

The dial thickness gauge 100 shown in FIG. 11 is configured such that mutually opposing contactors 102, 103 are provided at the end of U-shaped flexible arms 101, 101. When samples 1 to 3 are clamped between the contactors 102, 103, an indicating needle 105 of a dial 104 moves in accordance with the wall thickness of the samples 1 to 3 and points the scale corresponding to the wall thickness.

FIG. 9(2) shows the measurement errors $P_1$ to $P_3$, $R_1$ to $R_3$, $S_1$ to $S_3$, and $Q_1$ to $Q_3$ of the measurement data $J_1$ to $J_3$, $N_1$ to $N_3$, $M_1$ to $M_3$, and $K_1$ to $K_3$ respectively with respect to the reference data $I_1$ to $I_3$.

In reference to FIGS. 9(1), 9(2), the measurement errors $P_2$ to $P_3$, $R_2$ to $R_3$, $S_2$ to $S_3$ of the measurement data of wall thickness using the new type electrostatic capacity detectors 4 are sufficiently small compared to the measurement errors $Q_2$ to $Q_3$ of the measurement data of the wall thickness using the old type electrostatic capacity detector 9 to represent the relationships $P_2$, $R_2$, $S_2 < Q_2$ and $P_3$ $R_3$ $S_3 < Q_3$. Further, the smaller the radius of curvature R of the curved surface 50 of the sensor unit 5, the smaller the measurement errors $P_2$ to $P_3$, $R_2$ to $R_3$, $S_2$ to $S_3$ of the measurement data of the wall thickness using the new type electrostatic capacity detectors 4 become to represent the relationships $P_2 < R_2 < S_2$ and $P_3 < R_3 < S_3$.

Next, when comparing the measurement data $K_2$ of the wall thickness of the sample 2 with the radius of 30 mm using the old type electrostatic capacity detector 9 with the measurement data $K_3$ of the wall thickness of the sample 3 with the radius of 14 mm, the relationship of the measurement data is represented by $K_2 < K_3$. Also, the relationship of the measurement errors is represented by $Q_2 < Q_3$. This shows that when measuring the wall thickness of the square bottle 10A using the old type electrostatic capacity detector 9, the measurement value of the wall thickness of the corner portion 12 is smaller than that of the wall thickness of the facing portion 11 despite the fact that both the wall thicknesses are equal to each other. In contrast, when comparing the measurement data $J_2$, $N_2$, $M_2$ of the wall thickness of the sample 2 with the radius of 30 mm using the new type electrostatic capacity detector 4 with the measurement data $J_3$, $N_3$, $M_3$ of the wall thickness of the sample 3 with the radius of 14 mm, the relationship of the measurement data is represented by $N_3 < N_2$ and $M_3 < M_2$, and the relationship of the measurement errors is represented by $R_2 < R_3$ and $S_2 < S_3$. However, the relationship of the measurement data $J_2$, $J_3$ is represented by $J_2 \approx J_3$ and the relationship of the measurement errors is represented by P2≈P3. This shows that when measuring the wall thickness of the square bottle 10A with a wall thickness of 2 mm using the new type electrostatic capacity detector 4 equipped with the sensor 5 having the radius of curvature of 4 mm for the curved surface 50, the measurement values of the wall thickness of the facing portion 11 and the wall thickness of the corner portion 12 are almost equal to each other.

FIGS. 10(1), 10(2) show measurement data and measurement errors when measuring the wall thickness of each sample 1 to 3 with the wall thickness of 1 mm using the dial thickness gauge 100, the new type electrostatic capacity detector 4 having the radii of curvature R of 4 mm, 8 mm, and 10 mm for the curved surface 50 of the sensor unit 5, and the old type electrostatic capacity detector 9.

In reference to FIGS. 10(1), 10(2), the measurement errors $P_2$ to $P_3$, $R_2$ to $R_3$, $S_2$ to $S_3$ of the measurement data of wall thickness using the new type electrostatic capacity detector 4 are sufficiently small compared to the measurement errors $Q_2$ to $Q_3$ of the measurement data of the wall thickness using the old type electrostatic capacity detector 9, and are represented by $P_2$, $R_2$, $S_2 < Q_2$ and $P_3$ $R_3$ $S_3 < Q_3$. Further, the smaller the radius of curvature R of the curved surface 50 of the sensor unit 5, the smaller the measurement errors $P_2$ to $P_3$, $R_2$ to $R_3$, $S_2$ to $S_3$ of the measurement data of the wall thickness using the new type electrostatic capacity detectors 4 become to represent the relationships $P_2 < R_2 < S_2$ and $P_3 < R_3 < S_3$.

Next, when comparing the measurement data $K_2$ of the wall thickness of the sample 2 with the radius of 30 mm using the old type electrostatic capacity detector 9 with the measurement data $K_3$ of the wall thickness of the sample 3 with the radius of 14 mm, the relationship of the measurement data is represented by $K_2 < K_3$. Also, the relationship of the measurement errors is represented by $Q_2 < Q_3$. This shows that when measuring the wall thickness of the square bottle 10A using the old type electrostatic capacity detector 9, the measurement value of the wall thickness of the corner portion 12 is smaller than that of the wall thickness of the facing portion 11 despite the fact that both the wall thicknesses are equal to each other. In contrast, when comparing the measurement data $J_2$, $N_2$, $M_2$ of the wall thickness of the sample 2 with the radius of 30 mm using the new type electrostatic capacity detector 4 with the measurement data $J_3$, $N_3$, $M_3$ of the wall thickness of the sample 3 with the radius of 14 mm, the relationship of the measurement data is represented by $N_2 \approx N_3$, $M_2 \approx M_3$, and $J_2 \approx J_3$, and the relationship of the measurement errors is represented by $R_2 \approx R_3$, $S_2 \approx S_3$, and $P_2 \approx P_3$. This shows that when measuring the wall thickness of the square bottle 10A having a wall thickness of 1 mm using the new type electrostatic capacity detector 4, the measurement values of the wall thickness of the facing portion 11 and the wall thickness of the corner portion 12 are almost equal to each other.

Figure 12:
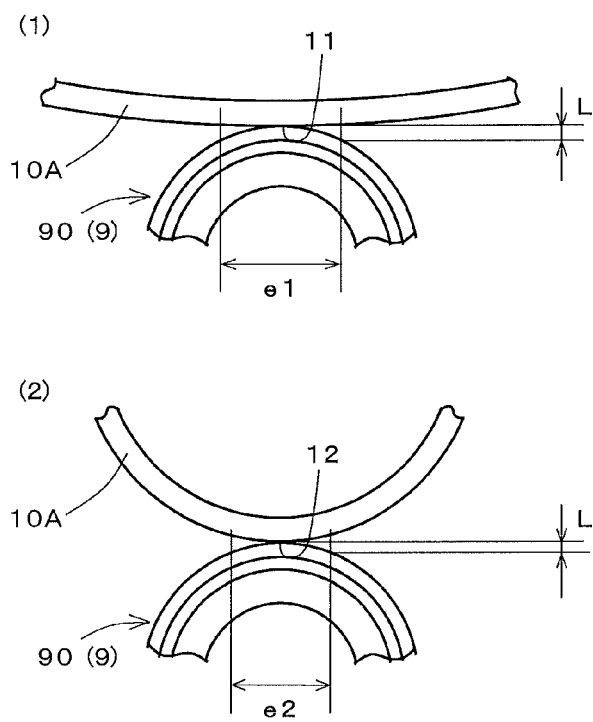
FIG. 12 is a view for illustrating a measurement state of a wall thickness using a conventional electrostatic capacity detector.

FIGS. 12(1), 12(2) show a state where the wall thickness of the square bottle 10A is being measured using the above-described old type electrostatic capacity detector 9. FIG. 12(1) shows a state where the sensor unit 90 is brought into contact with the facing portion 11 where the degree of curvature along the circumference direction is small, and FIG. 12(2) shows a state where the sensor unit 90 is brought into contact with the corner portion 12 where the degree of curvature along the circumference direction is large, respectively. Now, assuming that the electrostatic capacity in the area within a distance L from the surface of the square bottle 10A, the relationship between a measurement range e2 of the corner portion 12 and a measurement range e1 of the facing portion 11 is represented by e2<e1, and the ratio of both (e1/e2) becomes a value larger than 1. Since an electrostatic capacity is proportional to the area of an electrode, the measurement value of the wall thickness of the corner portion 12 becomes smaller than the measurement value of the wall thickness of the facing portion 11.

Figure 13:
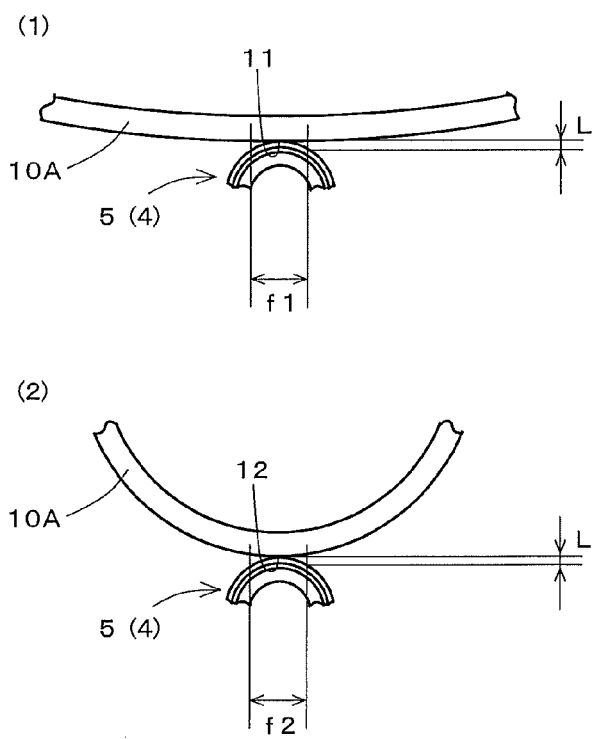
FIG. 13 is a view for illustrating a measurement state of a wall thickness using an electrostatic capacity detector according to the present invention.

FIGS. 13(1), 13(2) show a state where the wall thickness of the square bottle 10A is being measured using the new type electrostatic capacity detector 4 equipped with the sensor 5 having the radius of curvature R of 4 mm for the curved surface 50. FIG. 13(1) shows a state where the sensor unit 5 is brought into contact with the facing portion 11 where the degree of curvature along the circumference direction is small, and FIG. 13(2) shows a state where the sensor unit 5 is brought into contact with the corner portion 12 where the degree of curvature along the circumference direction is large, respectively. Now, assuming that the electrostatic capacity in the area within the distance L from the surface of the square bottle 10A, the relationship between a measurement range f2 of the corner portion 12 and a measurement range f1 of the facing portion 11 is represented by f2≈f1, and the ratio of both (f1/f2) becomes a value nearly equal to 1, and thus the measurement value of the wall thickness of the corner portion 12 and the measurement value of the wall thickness of the facing portion 11 are almost equal to each other.

As apparent from the above-described FIGS. 9, 10, 12, 13, the radius of curvature R of the curved surface 50 of the sensor unit 5 preferably has the least possible value, and the smaller the radius of curvature R, the closer become the measurement value of the wall thickness of the corner portion 12 and the measurement value of the wall thickness of the facing portion 11 to each other. However, the curved surface 50 of the sensor unit 5 needs to be manufactured, for example, by bonding the electrode sheet 7 onto the curved portion of the attachment substrate 51, and thus it is difficult to set the radius of curvature R to a value smaller than 2 mm in view of manufacturing techniques, manufacturing efficiency, and manufacturing costs, and therefore the lower limit of the radius of curvature R is set to 2 mm.

Meanwhile, when considering that the wall thickness of a glass bottle having the least thickness as a production standard is about 1 mm, the radius of curvature R of the curved surface 50 has the upper limit of 10 mm and is preferably set to a value no more than the upper limit. When the wall thickness of a sample made of a polyvinylidene fluoride (PVDF) with the same dielectric constant as the glass bottle having the thinnest wall thickness of 1.0 mm is measured using the old type electrostatic capacity detector 9 (R=17 mm), the measurement error is 0.5 mm (sample 3) as shown in FIG. 10(2). In this case, bottles with a wall thickness of 1.5 mm or less need to be disposed of as bottles with defect wall thickness, and thus the disposal of non-defective bottles is increased to cause practical problems. In contrast, when the above-described wall thickness of the sample 3 is measured using the new type electrostatic capacity detector 4 equipped the sensor 5 having the radius of curvature R of 10 mm for the curved surface 50, the measurement error is 0.3 mm (refer to FIG. 10(2)). The measurement error is further increased with the radius of curvature R exceeding 10 mm for the curved surface 50 of the sensor unit 5. Since this is not practical, the upper limit of the radius of curvature R is set to 10 mm. When considering both the manufacturing efficiency and the measurement errors on the basis of above descriptions, the radius of curvature R of the curved surface 50 of the sensor 5 is preferably set to about 4 mm, that is, greater than or equal to 3 mm and lower than or equal to 5 mm.

Figure 14:
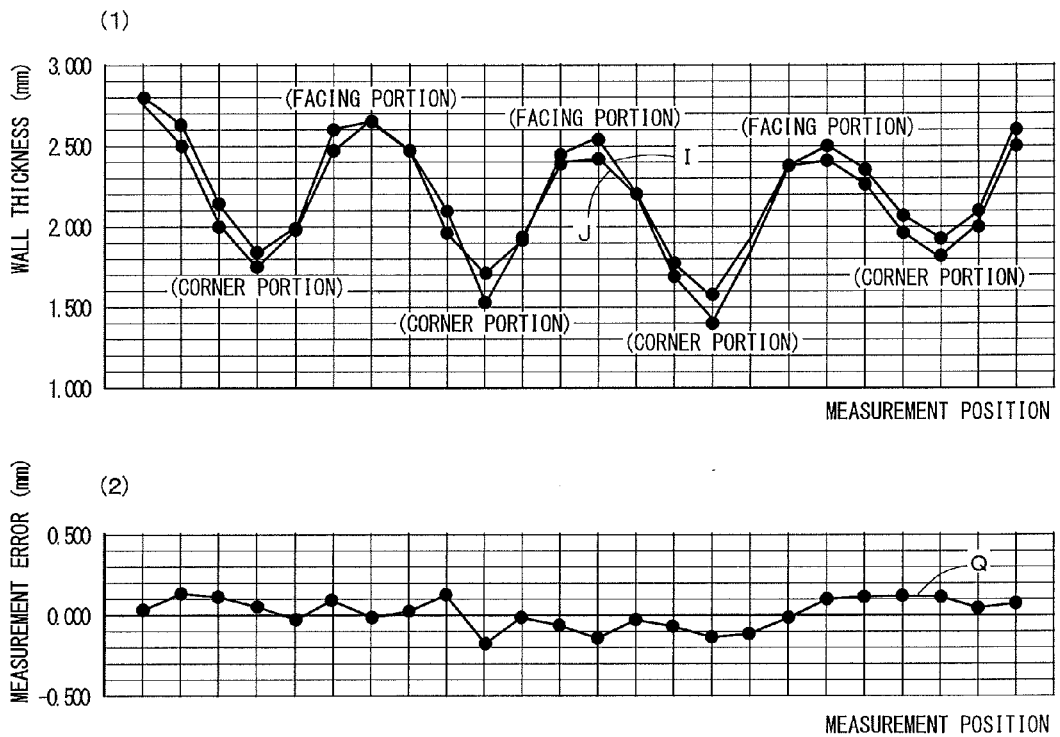
FIG. 14 is a view for illustrating measurement results of a wall thickness for the upper end portion of the body of a square bottle using an electrostatic capacity detector according to the present invention.
Figure 15:
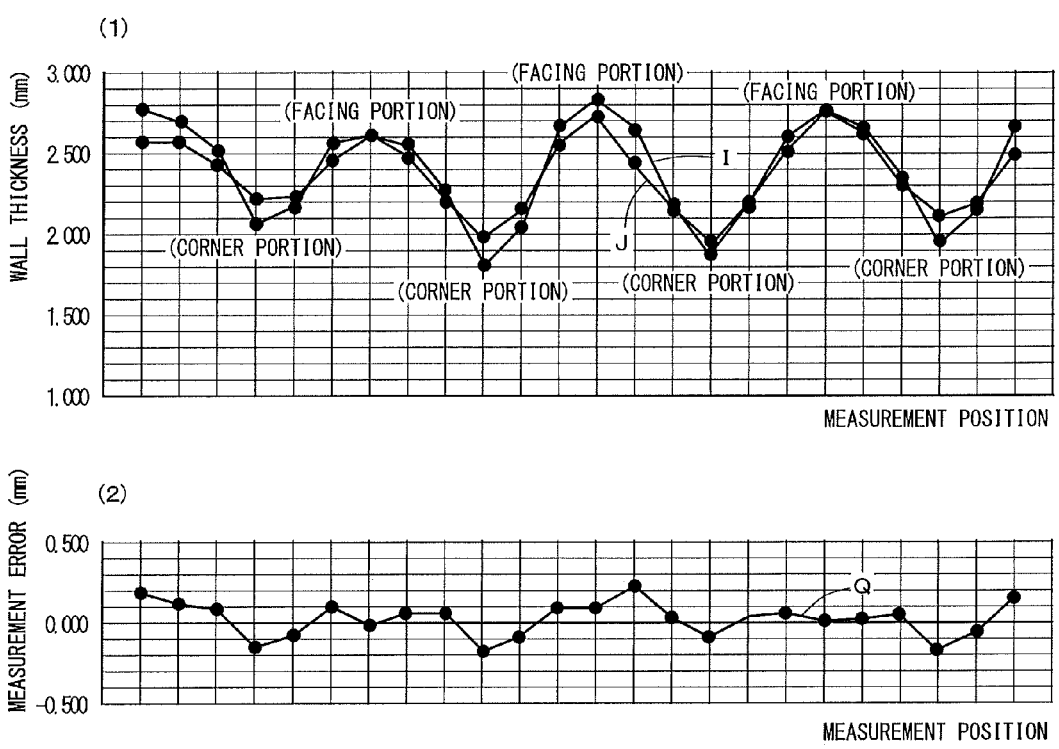
FIG. 15 is a view for illustrating measurement results of a wall thickness for the lower end portion of the body of a square bottle using an electrostatic capacity detector according to the present invention.

FIGS. 14 (1), 14(2) illustrate the measurement results of the wall thickness for the upper end portion of the body of the square bottle 10A over the entire periphery using the electrostatic capacity detector 4 equipped with the sensor 5 having the radius of curvature R of 4 mm for the curved surface 50. FIGS. 15 (1), 15(2) illustrate the measurement results of the wall thickness for the lower end portion of the body of the square bottle 10A over the entire periphery. In the drawings, a line graph I shows the measurement values (reference values) of the wall thickness over the entire periphery of a bottle acquired by measuring the wall thickness of the square bottle 10A at every prescribed angle using the above-described dial thickness gauge 100, and a line graph J shows the measurement values of the wall thickness over the entire periphery of a bottle acquired by measuring the wall thickness of the square bottle 10A at every prescribed angle using the new type electrostatic capacity detector 4 (R=4 mm). A line graph Q shows the measurement errors of the measurement values J with respect to the reference values I at every angle. Both the measurement errors at the facing portion 11 and the measurement errors at the corner portion 12 are limited to sufficiently small values for any of the upper end portion and the lower end portion of the body.

Figure 16:
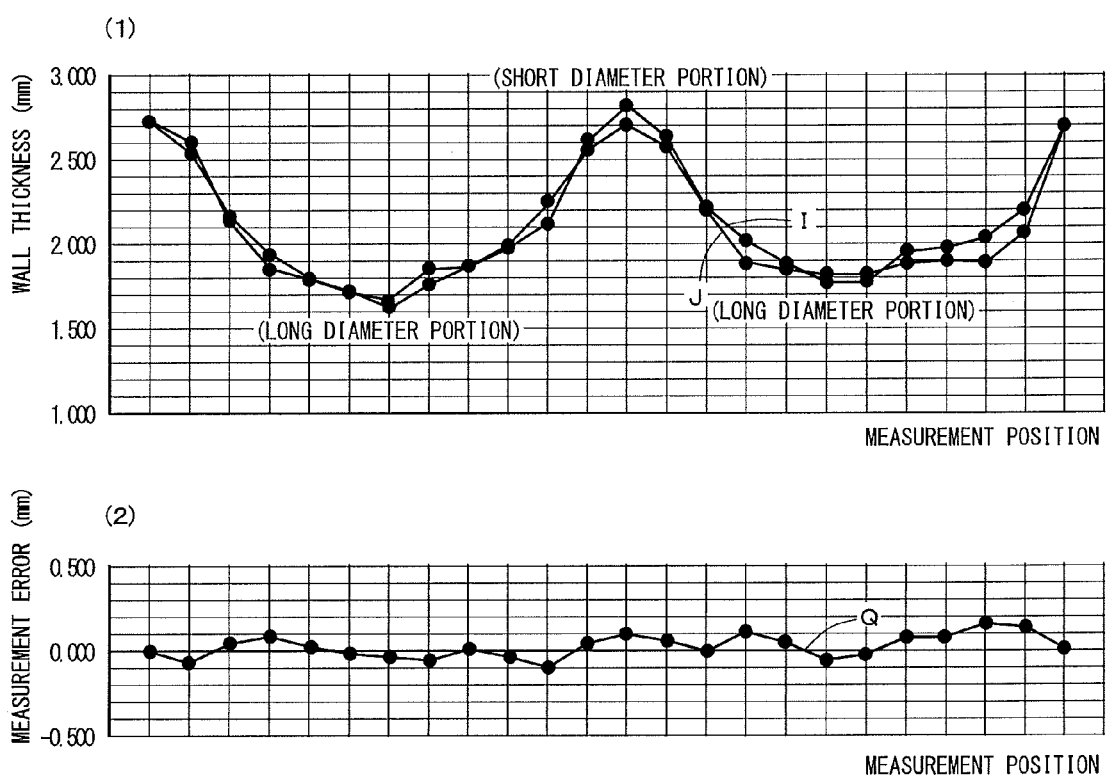
FIG. 16 is a view for illustrating measurement results of a wall thickness for an ellipse bottle using an electrostatic capacity detector according to the present invention.

Also, this is the case in the ellipse bottle 10B. FIGS. 16(1), 16(2) illustrate the measurement results of the wall thickness for the upper end portion of the body of the ellipse bottle 10B over the entire periphery using the electrostatic capacity detector 4 equipped with the sensor 5 having the radius of curvature R of 4 mm for the curved surface 50. In the drawing, the measurement errors are limited to sufficiently small values for any of the short diameter portion 13 and the long diameter portion 14 of the ellipse bottle 10B.

DESCRIPTION OF THE REFERENCE NUMERALS

1 Wall thickness inspection device
4 Electrostatic capacity detector
5 Sensor unit
6 Elastic body
7 Electrode sheet
10 Bottle
10A Square bottle
10B Ellipse bottle
50 Curved surface
51 attachment substrate
52 Curved portion
60 fulcrum
71 Measurement electrode pattern
72 Earth electrode pattern

The invention claimed is:

1. A wall thickness inspection device comprising: an electrostatic capacity detector for detecting the electrostatic capacity of a portion of an object subjected to wall thickness inspection, and an arithmetic and control unit for taking in the electrostatic capacity detected by the electrostatic capacity detector and converting the electrostatic capacity to a wall thickness, wherein the electrostatic capacity detector includes a sensor unit brought into contact with the surface of a portion of the object subjected to the wall thickness inspection, and an elastic body for biasing the sensor unit toward the portion of the object; the sensor unit has a curved surface with the radius of curvature R represented by 2 mm≤R≤10 mm; and the curved surface is formed by bonding an electrode sheet made of synthetic resin having each electrode pattern formed thereon to a belt-like attachment substrate so that at least the electrode pattern of a measurement electrode from among the electrode pattern of the measurement electrode and the electrode pattern of an earth electrode is positioned on the surface of a curved portion of the attachment substrate.

2. The wall thickness inspection device according to claim 1, wherein the electrode sheet is bonded to the attachment substrate from the front surface to the back surface thereof with each electrode pattern being formed so that the electrode pattern of the measurement electrode is located on the front surface of the attachment substrate and the electrode pattern of the earth electrode is located on the back surface of the attachment substrate.

3. The wall thickness inspection device according to claim 1, wherein the elastic body is formed of fan-shaped sponge or open-cell foam having a constant thickness; the attachment substrate is bonded to a first side end surface of the elastic body with the curved portion facing outside, and a second side end surface of the elastic body is bonded to a printed circuit board so that the whole of the elastic body expands and contracts with the pivot of the fan as a fulcrum.

* * * * *